(12) United States Patent
Sauerbrey et al.

(10) Patent No.: US 10,094,802 B2
(45) Date of Patent: Oct. 9, 2018

(54) HEATING SYSTEM FOR A MEASUREMENT CELL

(71) Applicant: EXIAS Medical GmbH, Graz (AT)

(72) Inventors: Werner Sauerbrey, Graz (AT); Josef Hindinger, Graz (AT)

(73) Assignee: EXIAS Medical GmbH, Graz (AT)

( * ) Notice: Subject to any disclaimer, the term of this patent is extended or adjusted under 35 U.S.C. 154(b) by 0 days.

(21) Appl. No.: 15/608,263

(22) Filed: May 30, 2017

(65) Prior Publication Data

US 2017/0350851 A1     Dec. 7, 2017

(30) Foreign Application Priority Data

Jun. 1, 2016  (DE) .................. 10 2016 110 106

(51) Int. Cl.
*B01L 3/00* (2006.01)
*G01N 27/416* (2006.01)
(Continued)

(52) U.S. Cl.
CPC ............ *G01N 27/416* (2013.01); *B01L 3/502* (2013.01); *G01N 33/49* (2013.01); *G01N 33/492* (2013.01); *G01N 33/4925* (2013.01); *B01L 2200/147* (2013.01); *B01L 2300/044* (2013.01); *B01L 2300/0627* (2013.01);
(Continued)

(58) Field of Classification Search
CPC .......... B01L 2200/12; B01L 2200/147; B01L 2300/0627; B01L 2300/0672; B01L 2300/0838; B01L 2300/0887; B01L 2300/123; B01L 2300/18; B01L 3/502; B01L 2300/044; B01L 2300/0645; B01L 2300/147; B01L 2300/1827; G01N 2035/00356; G01N 33/49; G01N 33/492;
(Continued)

(56) References Cited

U.S. PATENT DOCUMENTS 5,338,435 A * 8/1994 Betts .................. A61B 5/15003
204/406
5,342,498 A    8/1994 Graves et al.
(Continued)

FOREIGN PATENT DOCUMENTS

EP    1 674 866 A1    6/2006
EP    2 199 792 A1    6/2010
(Continued)

OTHER PUBLICATIONS

Extended European Search Report issued in parallel EP Application No. 17173886.7-1559 dated Sep. 6, 2017, 8 pages.

*Primary Examiner* — Jennifer Wecker
(74) *Attorney, Agent, or Firm* — Lewis Roca Rothgerber Christie LLP

(57) ABSTRACT

A measurement cell (3) for measuring at least one constituent of a liquid sample, in particular blood, includes a reception space (9) for receiving the sample includes a measurement system (8) having at least one sensor electrode (10) exposed within the reception space; a first heat supply equipment (12) extending over a first area (91); a second heat supply equipment (14) extending over a second area (93), the first and second heat supply equipment being arranged to heat the sample within the reception space (9), wherein the second area (93) is larger than the first area (91).

19 Claims, 6 Drawing Sheets

(51) Int. Cl.
*G01N 35/10* (2006.01)
*G01N 33/49* (2006.01)
*G01N 35/00* (2006.01)

(52) U.S. Cl.
CPC .............. *B01L 2300/0645* (2013.01); *B01L 2300/0672* (2013.01); *B01L 2300/0838* (2013.01); *B01L 2300/0887* (2013.01); *B01L 2300/123* (2013.01); *B01L 2300/18* (2013.01); *B01L 2300/1827* (2013.01); *G01N 35/1011* (2013.01); *G01N 35/1079* (2013.01); *G01N 2035/00356* (2013.01)

(58) Field of Classification Search
CPC ........... G01N 35/1011; G01N 35/1079; G01N 27/416
See application file for complete search history.

(56) References Cited

U.S. PATENT DOCUMENTS

| | | | |
|---|---|---|---|
| 5,786,608 A | 7/1998 | Lescouzeres et al. | |
| 5,916,425 A | 6/1999 | Leader et al. | |
| 6,679,279 B1 | 1/2004 | Liu et al. | |
| 7,195,036 B2 | 3/2007 | Burns et al. | |
| 7,332,130 B2 | 2/2008 | Handique | |
| 7,888,074 B2 | 2/2011 | Ehricht et al. | |
| 8,491,185 B2 | 7/2013 | Steinboeck et al. | |
| 2003/0155344 A1 | 8/2003 | Cobb | |
| 2004/0007275 A1 | 1/2004 | Hui Liu et al. | |
| 2004/0222091 A1* | 11/2004 | Lauks | B01L 3/502707 204/400 |
| 2006/0140822 A1* | 6/2006 | Krysl | G01N 27/403 422/108 |
| 2007/0286773 A1* | 12/2007 | Schlautmann | B01L 3/502707 422/68.1 |
| 2008/0121045 A1 | 5/2008 | Cole et al. | |
| 2009/0186404 A1 | 7/2009 | Kim et al. | |
| 2011/0056926 A1 | 3/2011 | Coursey | |
| 2013/0157271 A1 | 6/2013 | Coursey et al. | |
| 2014/0272927 A1 | 9/2014 | Coursey et al. | |
| 2015/0323555 A1 | 11/2015 | Kayyem et al. | |

FOREIGN PATENT DOCUMENTS

| | | |
|---|---|---|
| EP | 2 199 792 B1 | 8/2012 |
| WO | WO 01/02094 A1 | 1/2001 |
| WO | WO 2015/003722 A1 | 1/2015 |
| WO | WO 2016/004362 A1 | 1/2016 |

* cited by examiner

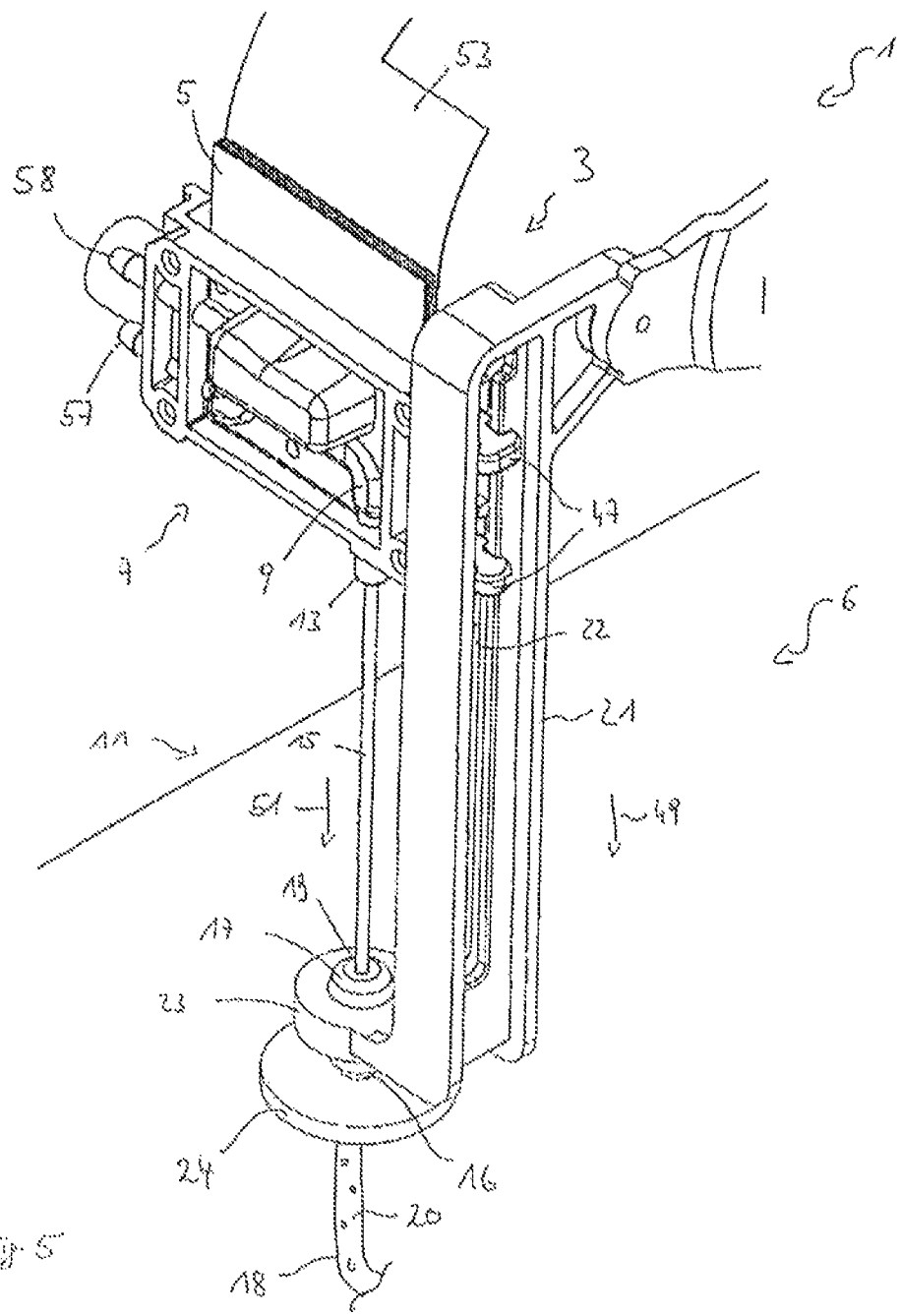

HEATING SYSTEM FOR A MEASUREMENT CELL

CROSS-REFERENCE TO RELATED APPLICATION(S)

This application is based upon and claims the benefit and priority of German Patent Application No. 10 2016 110 106.0, filed on Jun. 1, 2016, the entire contents of which are incorporated herein by reference.

FIELD OF INVENTION

The present invention relates to a measurement cell for measuring at least one constituent of a liquid sample, to a method for manufacturing a measurement cell, to a method for measuring at least one constituent of a liquid sample and to a measurement apparatus including the measurement cell.

ART BACKGROUND

For measuring parameters of a blood sample, such as blood gases, electrolytes and metabolites, an accurate control of the temperature of the sample to be examined may be required. Samples may be supplied into a conventional measurement apparatus at different temperatures, such as for example between 4° C. and 41° C. The measurement of the blood parameters is however required to be performed at a fixed temperature, such as for example 37° C. Such a temperature may for example be required to measure a partial pressure of oxygen, a partial pressure of carbon dioxide, to measure a pH or to measure an electrolyte concentration, such as calcium, sodium, potassium or chloride ions.

It may take some time to adjust the temperature of the sample to the intended measurement temperature. Furthermore, a measurement time is influenced by the time required to supply the sample into the measurement cell in the measurement apparatus. Further, the measurement time may be dependent on maximally possible pump velocities.

Furthermore, a measurement accuracy may depend on a possible change of the sample on the way from the external sample source to the measurement sensors due to carry-over effects (i.e. dilution). Also a possible entrapment of air bubbles may result in wrong measurements. The carry-over effects as well as the entrapment of air bubbles may most likely happen on positions where the material of the sample path changes. Different materials (e.g. steel, plastic, rubber, material of the sensor (casing) etc.) with which the sample may be in contact during supply to the measurement apparatus or during measurement itself may therefore influence the result of the measurement and thus may influence the measurement accuracy.

The required accuracy of the temperature regulation or temperature control may for example be 37° C.+/−0.2° C. Such accuracy of the temperature regulation may be required due to the temperature dependency of the solubility of gases within blood and within aqueous solutions, as well as the temperature dependency of the pH value for example. It may further be desired to use as little amount of sample as possible, while maintaining measurement accuracy. In this respect, the wetting properties of different materials of the measurement cell as well as the sample supply path may be relevant and also the constructional design of the measurement cell.

In conventional measurement systems, the sample may be heated along a pre-heating path which is integrated within the measurement apparatus. Other arrangements or concepts of the prior art directly heat up the sample within the measurement chamber by positioning the measurement cell or measurement chamber on or between temperature controlled heating blocks. Other systems of the prior art use measurement cells with sensor substrates having printed thereon resistance traces and a printed temperature sensor for changing and controlling the temperature of the sample, the measurement cell directly attached to the measurement apparatus in a fixed position.

EP 1 674 866 A1 discloses an arrangement for controlling the temperature of a measurement cell, wherein the measurement cell comprises a measurement channel in which a sensor element is arranged and an analyzer having a surface that can be temperature-controlled. The measurement cell can exchangeably be inserted into the analyzer and may be brought in contact with the surface which may be temperature-controllable. A heat conducting elastic or plastic layer is attached on a measurement cell wall or the surface which may be temperature-controllable.

EP 2 199 792 A1 discloses a method for examining the quality of a thermal coupling of a measurement cell, wherein the measurement cell is exchangeably insertable into an analyzer and comprises at least one sensor element within a measurement channel. The measurement channel is filled with a calibration liquid and a rapid temperature change is applied on the element which may be temperature-controllable and with which the measurement cell is in mechanical contact. Further, a time course of a signal of the at least one sensor element is acquired and the quality of the thermal coupling is determined based on an analysis of the time course of the signal.

U.S. Pat. No. 5,342,498 discloses an improved electronic wiring board having a thermistor and at least one blood gas sensor supported, in close relation, one to the other, on one side of the board and a heater supported on the other side of the board to provide heat in response to temperature sensed by the thermistor, to at least the region where the thermistor and the blood gas sensor are positioned on the board to control the temperature of the region of the board within a narrow distribution of temperatures.

U.S. Pat. No. 5,916,425 discloses an electronic wiring-substrate for sensors formed over a subminiature through-hole, wherein only a small amount of conductive material which fills each through-hole is in contact with each associated electrode. A relatively large number of sensors can be formed on the surface of the substrate within a relatively small fluid flow cell. This document also discloses a heater which is disposed within the substrate and which is capable of heating a blood sample and the array of sensors to a known stable temperature and maintaining that temperature as the sample is being analyzed, and a thermistor located in the sample path on the front side of the substrate. A number of sensors and independently controllable heaters (each one controlled by a thermistor) may be used to regulate the temperature of each sensor and the local temperature of the analyte at different locations along the flow path. The heater covers at least the area of the sample path.

A problem with the conventional systems and methods with a single heater in or on the sensor substrate is that the required temperature of the sample is not achievable in all situations in an acceptable time. In particular, when samples, for example blood, plasma, serum, have different temperatures, for example between 4° C. and 41° C., tempering the sample to a target temperature (for example 37° C.) and maintaining them at this temperature may not in all situations be possible in an acceptable time.

Other measurement systems and methods of the prior art have the disadvantage that a temperature controlled heating block and/or a pre-tempering path and/or a heated measurement chamber are used, to satisfy the requirements of the temperature control during the measurement. The heating block or the pre-tempering path are, due to cost issues, to be arranged within the measurement apparatus and cannot be placed into a consumable. Further, the thermal coupling between the heating block and the actual measurement cell is unknown and needs to be examined. The quality of the thermal coupling strongly influences the velocity or speed of arriving at a temperature of the sample that is required for the measurement.

Typical times to heat the sample to the desired target temperature conventionally are around 10 to 15 s. Using a pre-heating path may allow to reduce the time for achieving the desired target temperature, however, longer tubing is required Those skilled in the art know that this requires a higher sample volume due to carry-over effects and extends the time for the sample to be supplied to the measurement cell.

Another measurement system and method of the prior art has the disadvantage that a measurement cell with a heated sensor substrate is to be placed in a fixed position at the analyzer. This arrangement requires extended tubing paths, resulting in a higher sample volume, a higher demand of calibration liquids and a higher time effort for supplying these liquids.

In prior art solutions, the position of the measurement cell is fixed within or on the measurement apparatus. The supply of the sample thus necessarily is performed using extended tubing possibly resulting in a change/modification of the sample within the supply tubing. Further, the required minimal sample volume may be negatively affected. Due to the extensive tubing paths, also the minimally achievable measurement times are limited by a lower limit (for example 35 s) thereby lowering throughput.

There may be a need for a, in particular, movable measurement cell for measuring at least one constituent of a liquid sample, for a measurement system for measuring at least one constituent of a liquid sample, for a method for manufacturing a measurement cell and for a method for measuring at least one constituent of a liquid sample, wherein at least one of the above-mentioned disadvantages of the prior art are attenuated, reduced or even avoided.

In particular, it may be desired to provide a measurement cell that allows accurate and fast tempering of a sample and which at the same time enables accurate measurements on the sample, in order to measure at least one constituent. The measurement cell should be cheap to be placed in a consumable and should be independent of any other external heating devices to be placed in a position which allows the minimal possible sample path length.

The need may be satisfied by the subject-matter of the independent claims. The dependent claims specify particular embodiments of the present invention.

SUMMARY OF THE INVENTION

According to an embodiment of the present invention, it is provided a measurement cell for measuring at least one constituent of a liquid sample, in particular blood, plasma or serum, the measurement cell including: a reception space for receiving the sample; a measurement system having at least one sensor electrode exposed within the reception space; a first heat supply equipment extending over a first area; a second heat supply equipment extending over a second area, the first and second heat supply equipment being arranged to heat the sample within the reception space, wherein the second area is larger than the first area.

The measurement cell may in particular be a movable measurement cell, representing a consumable of a measurement apparatus that is replaced frequently. The measurement cell, in particular the measurement system, may be adapted to determine at least one property of the constituent, such as concentration, partial pressure or the like. The measurement system may therefore in particular comprise several sensor electrodes for measuring different properties of the sample or for measuring different constituents of the sample.

The measurement system may in particular be adapted to measure the concentration of at least one ion, such as $K^+$, $Ca^{++}$, $Na^+$, $Cl^-$, and/or pH and/or partial pressures of $O_2$, $CO_2$ and/or concentrations of Glucose, Lactate, Urea, Creatinine or the like. For each particular analyte, at least one separate respective sensitive area may be provided. When several sensitive areas for measurement of different constituents of the liquid are provided, the sensitive area may be arranged side by side along a longitudinal direction of the reception space.

The measurement system may be adapted to perform potentiometric and/or amperometric measurement and/or conductometric measurements i.e. measurements of electrical potentials and/or electric currents and/or electric impedances. As measurement result, concentration of different analytes may be determined and/or the values of the partial pressures of different gases within the sample may be determined and/or the volumetric amount of blood cells and output. The measurement system may alternatively or additionally also be adapted to perform optical measurements.

The reception space may in particular be configured as a channel having a longitudinal direction corresponding to a flow direction during supply of the sample into the reception space.

The first heat supply equipment and the second heat supply equipment both may provide heat energy that may be conducted via radiation and/or diffusion towards the sample within the reception space. For activating the heat supply equipments, such as supply an electric energy, the measurement cell may comprise further components, such as an electric energy supply and a controlling system.

The first heat supply equipment may primarily be formed and shaped to heat the sample within the reception space due to its proximity to the reception space. The second heat supply equipment may heat also other components of the measurement cells being spaced apart from the reception space. The second heat supply equipment may have also a larger heating power than the first heat supply equipment. In particular, the heating power of the heat supply equipment may be at least appropriately proportional to the respective area size. Having the first heat supply equipment and the second heat supply equipment may allow to reduce the time to reach a desired target temperature of the sample and to maintain this target temperature. The second heat supply equipment may be operated to achieve a target temperature of a large portion of the measurement cell, in particular in an operational mode, in which no measurement on a sample is performed.

The first heat supply equipment may be arranged in immediate proximity to the reception space (also called measurement channel). For example, 10 μm to 80 μm electrical isolation material may be between the first heat supply equipment and the reception space. The first heat supply equipment may be utilized to locally heat the sample, without substantially heating other portions of the measurement cell.

The first heat supply equipment and the second heat supply equipment may be independently controllable by a control system. In a projection perpendicular to a first plane in which the first area is arranged, the first heat supply equipment may overlap with the second heat supply equipment. Thus, the second heat supply equipment may also heat the reception space (as the first heat supply equipment) but may additionally also heat other portions of the measurement cell.

In particular embodiments of the present invention, the measurement cell may comprise, in different regions of the measurement system or in different regions of different sensor electrodes of the measurement system, each a first heat supply equipment and a second heat supply equipment, in order to heat areas close to the respective sensor electrodes to different temperatures. Also in this embodiment, the first heat supply equipment and the associated second heat supply equipment in a particular region of a particular sensor electrode may overlap in projection, such that both, the respective first heat supply equipment and the respective second heat supply equipment heat the respective region of the reception space.

According to an embodiment of the present invention, the second area is between two times and ten times, in particular between three times and five times, as large as the first area. Having a relatively large second area may advantageously allow to heat a relatively large portion or volume of the measurement cell to, or close to the target temperature in a stationary condition, where no measurement is performed on a sample. Introduction of a sample to be measured only into the reception space will disturb the homogeneous temperature distribution across the second area only slightly. Thus, it may be easily achievable to level the inhomogeneous temperature distribution or to reduce the disturbance from the homogeneous temperature distribution According to an embodiment of the present invention, the first heat supply equipment is arranged closer to the reception space than the second heat supply equipment. When the first heat supply equipment is arranged closer to the reception space than the second heat supply equipment, a local temperature deviation from a homogeneous temperature distribution may easily be counteracted by activating or operating the first heat supply equipment, in particular in combination with the second heat supply equipment. In particular, the first area may be formed and arranged such that the first heat supply equipment may counteract efficiently a drop of the temperature due to introduction of a liquid sample into the reception space.

According to an embodiment of the present invention, a shape of a sectional view of the reception space, at least in a region wherein the at least one sensor electrode is located, resembles a shape of the first area. When the shape of the sectional view of the reception space substantially resembles a shape of the first area, the first heat supply equipment may effectively locally heat the sample contained within the reception space, i.e. heats an area or a volume which is expected to have a temperature different from the target temperature, when the sample is introduced into the reception space.

According to an embodiment of the present invention, an area size of a sectional extent of the reception space, at least in a region where the at least one sensor electrode is located, is between 0.3 and 5 times, in particular 0.5 to 3 times, further in particular 0.75 to 1.5 times, still further in particular 0.9 to 1.1 times, even still further 0.95 to 1.05 times a size of the first area.

When the area sizes of the sectional extent of the reception space substantially equals or corresponds to the size of the first area, the risk is reduced that, when the first heat supply equipment is activated (thus supplies heat energy) that areas surrounding the reception space are overheated due to lower heat capacities than the liquid samples, that bears the risk that, due to thermal conduction, also the sample within the reception space at least temporarily overheats. Thereby temperature oscillation can be reduced and thus a fast heating to the target temperature may be reliably achieved.

According to an embodiment of the present invention, the first heat supply equipment comprises at least one first conductive path formed in a meander shape and extending substantially in a first plane and/or wherein the second heat supply equipment comprises at least one second conductive path formed in a meander shape and extending substantially in a second plane substantially parallel to the first plane and offset from the first plane in a direction orthogonal to the first plane.

The first heat supply equipment may comprise several first conductive paths and/or the second heat supply equipment may comprise several second conductive paths. The respective conductive paths may advantageously be manufactured according to conventional printed circuit board manufacturing techniques which allow application of particularly shaped copper traces onto a substrate. When the conductive paths have a meander shape, they may in a homogeneous manner heat the respective first area or second area. In particular, the second conductive path may comprise sections of copper traces that run parallel to each other. Also the first conductive path may comprise sections of copper traces that run parallel to each other. Thereby, the first heat supply equipment and the second heat supply equipment may easily be realized using conventionally available manufacturing techniques.

The first plane may be closer to the reception space than the second plane. The planar arrangement of the conductive paths may also simplify the manufacturing.

According to an embodiment of the present invention, the measurement system comprises plural sensor electrodes arranged substantially in a sensor electrodes plane that is closer to the first plane than to the second plane. In particular, the reception space may be limited by a planar bottom which is partly formed by the plural sensor electrodes, such that the plural sensor electrodes are exposed within the reception space, in particular exposed at the bottom of the reception space.

According to an embodiment of the present invention, a temperature sensor is arranged to measure a temperature related to the sample.

The temperature sensor may allow to monitor the temperature related to the sample, in particular to monitor the temperature of the sample within the reception space. When the temperature sensor is not directly arranged within the reception space, but spaced apart from the reception space such that the temperature sensor is not directly in contact with the sample, the temperature sensor may be calibrated in order to estimate or derive the actual temperature of the sample from the temperature measured by the temperature sensor.

Temperature detection may be performed by measuring a resistance of the first and/or second conductive path or trace, wherein the resistance may depend on the temperature. The conductive path(s) may be arranged in the meandering manner such that the heating conductive trace multiple times crosses (when viewed in projection) the measurement channel, without electrically contacting a sample within the reception space. Thereby, a homogeneous temperature profile, in particular constant temperature, along the longitudinal direction of the measurement channel may be achieved.

Thereby, the measurement accuracy may be improved. The desired temperature, achievable in embodiments of the present invention, may for example be 37° C. The accuracy of the temperature control may for example achieve a temperature of 37° C.+/−0.2° C.

According to an embodiment of the present invention, a sensing region of the temperature sensor is located within the reception space. In this embodiment, the temperature sensor may directly measure the temperature of the sample. Anyway, calibration of the sensor may be required, to obtain an absolute temperature of the sample. This can be achieved by other reference sensors.

According to an embodiment of the present invention the measurement cell further comprises a reference temperature sensor having a nominal reference (electrical) resistance (e.g. a resistance at 25° C.) that is larger than, in particular between 10 times and 1000000 times, further in particular between 100 and 10000 times, a nominal resistance (e.g. a resistance at 25° C.) of the temperature sensor.

Due to the higher reference nominal resistance measurement voltages (such as voltage drops caused by the resistor) of the reference temperature sensor may be much larger than measurement voltages of the temperature sensor that may be in a range of micro Volts. Thus, the reference temperature sensor may be less affected by unpredictable influences, that may affect factory calibration. Advantageously, the temperature sensor may be calibrated (e.g. when the whole measurement cell is maintained at 37° C.) using the reference temperature sensor. Thereby the temperature measurement of the sample may be improved regarding accuracy.

According to an embodiment of the present invention, a sensing region of the temperature sensor is formed by the first conductive path, the first conductive path being selectively, in particular alternatingly, operable as heat producing or temperature measuring.

Thus, according to this embodiment, the first conductive path (forming the first heat supply equipment) can advantageously be used for two different purposes, namely for heating and for sensing the temperature. An appropriate control system may be connected to the first conductive path and may switch between the different functions of the first heat supply equipment. In this embodiment, a (relative) calibration, in particular regarding a difference between the temperature prevailing at or within the sample and the temperature prevailing at the temperature sensor, of the temperature sensing function may be required, since the first conductive path is not in direct contact with the sample to be measured, but is isolated from the sample, for example by an isolating layer. Further, an absolute calibration may be performed to ensure that the temperature measured by the temperature sensor is (at least substantially) the actual temperature at the temperature sensor. After the calibration(s) the calibrated measured temperature may truly reflect the temperature at or within the sample.

According to an embodiment of the present invention, the sensor electrodes of the measurement system, the first conductive path, in particular first copper trace, and the second conductive path, in particular second copper trace, are formed on or in different insulating layers that are attached to each other to form a layer stack portion (of the measurement cell), the insulating layers in particular being formed from a polymer, wherein the polymer in particular comprises a fibre-reinforced polymer, fibres of the fibre-reinforced polymer in particular including at least one of glass, carbon, aramid, basalt, paper, wood, asbestos, wherein the polymer in particular comprises at least one of epoxy, vinylester, polyester thermosetting plastic, phenol formaldehyde. By providing different layers, the manufacturing of the measurement cell may be simplified.

According to an embodiment of the present invention, the measurement cell further comprises a temperature controller, adapted to receive a temperature measurement signal from the temperature sensor, to adjust a heating power of the first heat supply equipment and/or the second heat supply equipment, wherein the temperature controller is selectively operable in a first operation mode and a second operation mode, wherein in the first operation mode the second heat supply equipment is feedback controlled based at least on the temperature measurement signal such that a target temperature of the sample in the reception space is reached, without supplying heating power from the first heat supply equipment to the sample. In the second operation mode the first heat supply equipment and the second heat supply equipment are activated in response to a temperature drop indicated by the temperature sensor, to supply a (particular amount of) heating energy to the sample, the heating energy being derived from a size of the temperature drop.

Thus, the temperature controller is adapted to either feedback control the second heat supply equipment or, without feedback control from the temperature sensor, activate the first and/or second heat supply equipment, for example for a particular time and with or associated with a particular heating power. A particular sample volume may be introduced into the reception space when a sample is to be measured. Using the temperature drop, the volume of the sample and the heat capacity of the sample may allow to calculate a heat energy to be supplied to the sample, in order to heat the sample to the target temperature. This heat energy may be distributed between the first and second heat supply equipment and corresponding electrical energy may be supplied to the respective heat supply equipment. Thereby, a fast heating of the introduced sample may be achieved, without risking an overheating of the sample.

According to an embodiment of the present invention, the measurement system is adapted to perform potentiometric and/or amperometric measurement and/or conductometric measurements i.e. measurements of electrical potentials and/or electric currents and/or electric impedances. Other measurements, especially optical measurements, such as absorption and/or optical activity/dichroism and/or fluorescence measurements may be possible.

According to an embodiment of the present invention, the measurement cell further comprises a cover portion connected to the layer stack and limiting the reception space above the layer stack. The cover portion may in particular be integrally formed, further in particular manufactured by injection moulding, still further in particular using polycarbonate, polyester, polyamides polyacrylnitrile, polyacrylates, polyolefines, polymetharylates, copolymers and blends thereof. Thus, the reception space may partly be limited by a top layer of the layer stack, namely the layer which comprises the sensor electrodes of the measurement system, and may partly be limited by a section of the cover portion (of the measurement cell). Also 3D-printing techniques and/or milling techniques and/or moulding techniques etc may be employed According to an embodiment of the present invention, the measurement cell is configured as a flow through cell, having an inlet and an outlet both in communication with the reception space and both in particular formed at the cover portion, further in particular formed integrally with the cover portion. Thereby, introduction of a sample, washing the cell and introducing another sample may be enabled.

According to an embodiment of the present invention, the measurement cell further comprises a sample supply system attached to an inlet to allow supply of a liquid sample into the reception space, wherein the sample supply system includes a supply needle connected at one end to the inlet, the supply needle having a lumen in communication with the reception space.

The sample supply system may be fixedly attached to the inlet, not allowing deformation or movement. The sample supply system may be made from solid and/or non-bendable material(s) and may be stiff. The sample supply system may be adapted to supply a fluid sample to the reception space from a sample container providing access to a surface of the liquid sample, in particular without requiring any (bendable or flexible) tubing or any elastomeric sealing. The supply system may not change shape and/or may not deform during supply of the sample into the reception space.

The movable measurement cell may in particular be moved for feeding a sample from an external source via the sample supply system and the inlet of the measurement cell into the reception space. Different sample source containers or external equipment providing the sample may require different orientations or configurations of the sample supply system in order to be able to feed the sample from the external source into the reception space. The sample supply system may be fixedly attached to the inlet (in one embodiment being arranged at the second portion of the measurement cell, in another embodiment being arranged at the first portion of the measurement cell). Thus, during feeding a sample from different sample sources, the sample supply system remains attached to the inlet in a position and orientation fixed relative to the rest of the measurement cell. However, the whole measurement cell may be moved (for example translated and/or rotated or turned) in order to arrange the sample supply system (in particular regarding orientation) such that the sample can be filled from the external source or external container into the sample supply system which in turn supplies the sample via the inlet into the reception space for measurement.

The sample supply system allows supplying a sample from different source containers into the reception space via for example a supply tube, such as a supply needle made from an inert metal or any (in particular biocompatible) material matching the requirements for this application, e.g. some polymeric material. Thereby, deterioration of the sample may be reduced and the supply length may be limited to the length of the sample supply system. The sample supply system may include a supply needle connected at one end to the inlet having a lumen in communication with the reception space.

The supply needle may be straight and may have a length between 3 cm and 20 cm. Thereby, a short supply length may be provided. For feeding a sample from an external container into the reception space, another end of the supply needle may be immersed into the sample contained in an open external container, while the other end of the supply needle is vertically arranged at a lower level than the one end of the needle that is connected to the inlet. For feeding a sample from other external sources, the supply needle may be oriented differently, for example such that the one end is vertically at a lower level than the other end of the supply needle. Thereby, samples from different sample sources may conveniently be fed into the reception space for measurement by previously appropriately orienting/positioning (i.e. moving in general) the movable measurement cell.

According to an embodiment of the present invention, the sample supply system further includes an elastomer element having a through hole, the supply needle being at least partially inserted into the through hole. The supply needle is in a fixed orientation coupled to the first and/or second portion.

The elastomer may comprise rubber and the elastomer element may in particular have (optionally in some embodiments) a rotational symmetry, the symmetry axis in particular running along a longitudinal axis of the through hole. In other embodiments the elastomer element does not have any symmetry. The elastomer element may, when engaged into a supporting portion, support and protect the supply needle. Furthermore, the elastomer element may allow connection of a capillary, while the supply needle is at the other end partly inserted into the through hole such that the other end of the needle and an end of the capillary contact each other (or are at least close apart from each other) at a center of the through hole, thereby allowing feeding a sample originally located within the capillary into the supply needle for supply of the sample into the reception space.

According to an embodiment of the present invention, the supply needle is adapted to allow supply of a sample from a syringe or from a vacutainer, wherein the supply needle being partially inserted into the through hole of the elastomer element from one side allows supply of a sample from a capillary while the capillary is partially inserted into the through hole of the supply needle from another side. Thereby, a number of conventionally used sample containers or sample source equipment is supported.

According to an embodiment of the present invention, it is provided a measurement apparatus for measuring at least one constituent of a liquid sample, the measurement apparatus comprising: a (in particular movable) measurement cell according to one of the preceding embodiments further comprising a trail engagement portion; a mounting system for movably mounting the movable measurement cell, the mounting system including: a bar having a guiding trail; and a supporting portion at one end of the bar for supporting the supply needle, wherein the trail engagement portion of the measurement cell is engageable with the guiding trail for moving the movable measurement cell in a direction of the guiding trail being along a longitudinal direction of the supply needle.

The measurement apparatus may further comprise a data processing module for processing measurement data obtained from the measurement system, an energy supply system for providing electrical energy to components (such as the measurement system, heating/temperature detection system(s)) of the measurement cell, pump(s), valve(s), a user interface, external network capability, access to a database, etc.

The bar may also be formed as a frame allowing to move the movable measurement cell along a straight translation path and also allowing the swivel or rotate of pivot the measurement cell. The moving distance may amount to between 3 cm and 15 cm, the cell may be rotated by 10 to 90 degrees or even further. The bar may have a length between 3 cm and 15 cm. The measurement cell engaged with the guiding trail may be shifted (for example by hand) along the guiding trail. The measurement cell may for example comprise as trail engagement portion one (or more)

protrusions (in particular integrally formed with the second portion) being inserted into and/or protruding through a slit representing the guiding trail. Other configurations are possible. When the measurement cell is shifted towards another end of the bar, the trail engagement portion may be disengaged from the guiding trail for removing the measurement cell from the mounting system. For example, when the guiding trail is provided as a slot, the slot may have at the other end of the bar, an enlarged opening through which ends of the trail engagement portion of the measurement cell may be withdrawn for removal of the measurement cell (e.g. for maintenance or replacement). Also the bar may be manufactured from a polymer, in particular manufactured using injection moulding.

It should be understood that features individually or in any combination disclosed, provided or applied to the measurement cell or measurement apparatus may also, individually or in any combination applied to a method for manufacturing a measurement cell or a method for measuring at least one constituent of a liquid sample, according to embodiments of the present invention and vice versa.

According to an embodiment of the present invention, it is provided a method for manufacturing a measurement cell for measuring at least one constituent of a liquid sample, the method comprising: arranging a first heat supply equipment extending over a first area on a first insulating layer; arranging a second heat supply equipment extending over a second area on a second insulating layer, the second area being larger than the first area; arranging at least one sensor electrode of a measurement system on a top insulating layer; stacking the first layer on top of the second layer; stacking the top layer on top of the first layer; and forming a reception space for receiving the sample above the top layer by attaching a cover portion onto the top layer such that the sensor electrode is exposed within the reception space. Thereby, conventional manufacturing techniques may be utilized.

According to an embodiment of the present invention, it is provided a method for measuring at least one constituent of a liquid sample, the method comprising: receiving the sample in a reception space; heating the sample selectively using a first heat supply equipment extending over a first area and/or a second heat supply equipment extending over a second area, wherein the second area is larger than the first area; and measuring a property of the constituent using a measurement system having at least one sensor electrode exposed within the reception space.

The measuring method may, prior to receiving the sample in the reception space, comprise to operate exclusively the second heat supply equipment, without operating or activating the first heat supply equipment, in order to achieve a target temperature. Once the sample is injected or introduced into the reception space, this may be monitored in an automatic manner. In other embodiments the user may switch to a second operational mode provided for measuring the sample. In this second operation mode, a temperature drop detected by the temperature sensor is associated with a cooling caused by the received sample. In order to heat the sample received in the reception space, both, the first heat supply equipment and also the second heat supply equipment are activated for a relatively short amount of time (e.g. shorter than 2 s), in order to supply a particular heat energy, as derived or calculated based on the temperature drop. After applying this heat energy (in particular without feedback from the temperature sensor), the measurement cell may switch back to a feedback control operating mode, wherein exclusively the second heat supply equipment is operated feedback controlled by measurement signals of the temperature sensor.

Within or just below the reception space (also called sample channel), a temperature sensor may be arranged which monitors the temperature within the measurement channel. The temperature determination may alternatively also be performed using the first conductive path of the first heat supply equipment. In this embodiment, the first heat supply equipment, in particular first conductive path, is operated alternatingly for heating and temperature measuring. Since using the first heat supply equipment, an energy supply is locally limited to the regions which are cooled by the introduced sample, the risk of overheating due to thermal equilibration is reduced. In particular, an uncontrollable energy supply from other areas of the measurement cell which are overheated may be reduced. After switching off or reducing the heating power of the first heat supply equipment, a further temperature increase is not to be expected, since after switching off the first heat supply equipment, an immediate discharge of heat energy in the adjacent cooler portions of the measurement cell occurs. Thus, the time for adjusting the temperature of the sample to a target temperature may considerably be reduced compared to conventional solutions. The time to adjust the sample to the target temperature may for example be below 5 s, in particular between 2 s and 5 s.

BRIEF DESCRIPTION OF THE DRAWINGS

Embodiments of the present invention are now described with reference to the accompanying drawings. The invention is not restricted to the described or illustrated embodiments.

FIG. 5 schematically illustrates a measurement apparatus according to an embodiment of the present invention in a perspective view including a measurement cell according to an embodiment of the present invention;

DETAILED DESCRIPTION

Figure 1:
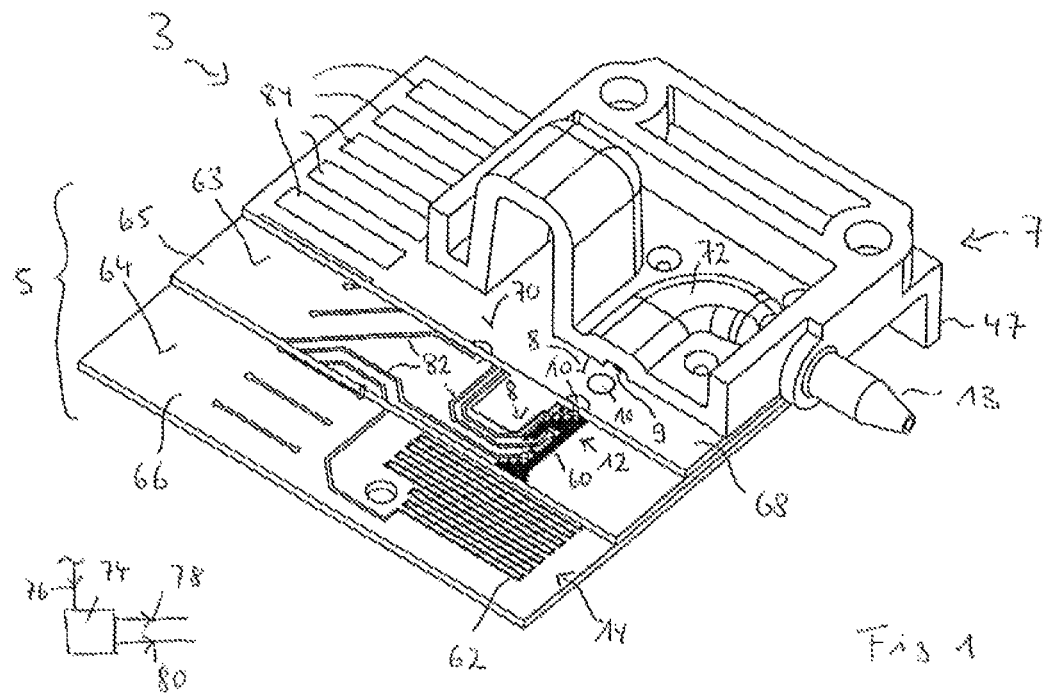
FIG. 1 schematically illustrates in a partially cut-out, perspective view a measurement cell according to an embodiment of the present invention.
Figure 2:
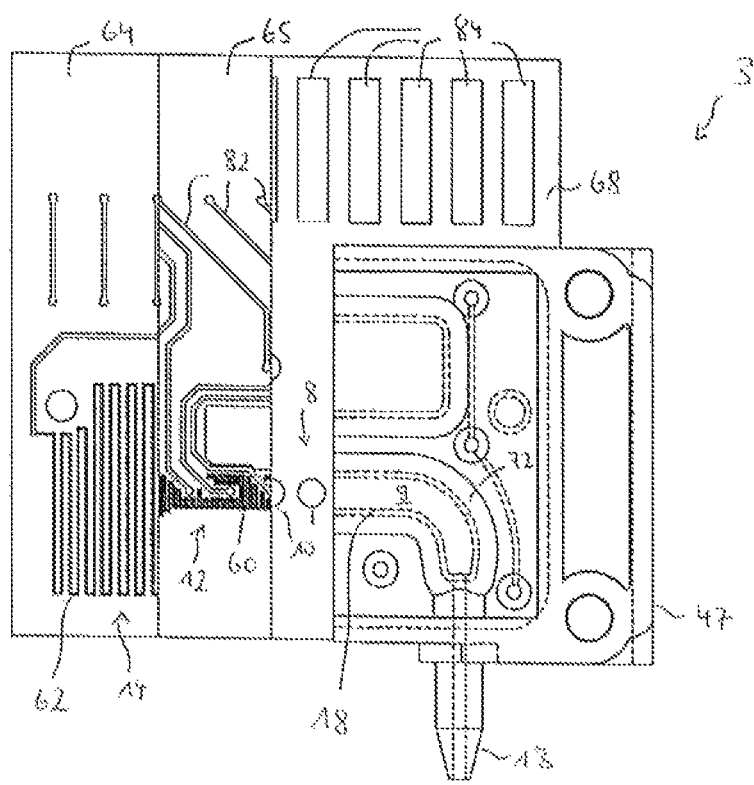
FIG. 2 illustrates the measurement cell illustrated in FIG. 1 in a plan view.

The measurement cell 3 illustrated in FIG. 1 in a partially cut-out, perspective view includes a reception space 9 for receiving a liquid sample. FIG. 2 illustrates a respective plan view. The measurement cell 3 further includes a measurement system 8 having at least one sensor electrode 10 exposed within the reception space 9. The measurement cell 3 further includes a first heat supply equipment 12, which extends over a first area which will be described with reference to FIG. 4 below. The measurement cell 3 further includes a second heat supply equipment 14 extending over a second area, which will also be described with reference to FIG. 4. Thereby, the first heat supply equipment 12 and the second heat supply equipment 14 are arranged, i.e. spatially located, close in thermal contact with the sample when introduced into the reception space 9. A shape of a sectional view of the reception space 9 is labeled in FIG. 2 with reference sign 18.

The second area of the second heat supply equipment 14 is larger than the first area of the first heat supply equipment 12. The first heat supply equipment 12 comprises at least one first conductive path 60, as is illustrated in FIG. 2 illustrating a plan view of the measurement cell 3 illustrated in FIG. 1. The first conductive path 60 (extending substantially in a first plane 63) is formed in a meander shape comprising several sections of copper traces running parallel to each other, in projection crossing the reception space 9. The first conductive path 60 of the first heat supply equipment 12 extends in a first plane, which lies in the surface 63 of the first layer 65 on which the first conductive path 60 is arranged.

Also the second heat supply equipment 14 comprises at least one second conductive path 62 formed in a meander shape and extending substantially in a second plane 64 which corresponds substantially to the surface of the second layer 66 on which the second conductive path 62 is formed. The first plane 63 is thereby offset from the second plane 64 and the first plane 63 is closer to the reception space 9 than the second plane 64.

The sensor electrodes 10 are arranged on a top layer 68, wherein the top layer 68 has a surface 70, which, together with the sensor electrodes 10, forms a bottom of the reception space 9, thus limiting the reception space 9 at the bottom. From above, the reception space 9 is covered by a wall section 72 of a cover portion 7 of the measurement cell 3. The surface of the top layer 68 lies in the sensor electrodes plane of the sensor electrodes 10.

The measurement cell 3 further comprises a trail engagement portion 47 for engaging the measurement cell 3 at a guiding trail which will be described with reference to FIG. 5.

For introducing a sample into the reception space 9, the measurement cell 3 comprises an inlet 13. The inlet 13 of the measurement cell 3 is integrally formed with the cover portion 7 of the measurement cell 3. An outlet of the measurement cell is not illustrated in FIGS. 1, 2 but is illustrated in FIG. 5 and described below.

For operating the first heat supply equipment 12 and the second heat supply equipment 14, the measurement cell 3 includes a temperature controller 74 which is adapted to receive a measurement signal 76 from a temperature sensor (not explicitly illustrated in FIGS. 1 and 2) which may also be comprised within the measurement cell 3 and which may be arranged to measure a temperature related to the sample within the reception space 9.

The temperature controller 74 is further adapted to adjust a heating power of the first heat supply equipment 12 and the second heat supply equipment 14, in particular by providing respective control signals 78 and 80 to the respective heat supply equipment. The temperature controller is operable in a first operation mode and a second operation mode. The first operation mode may correspond to a stationary condition, in which no sample is introduced into the reception space and no measurement or calibration is performed. In this first operation mode, the temperature controller 74 feedback controls the second heat supply equipment 14 based at least on the temperature measurement signal 76 such that a target temperature (for example 37° C.±0.2° C.) of the liquid in the reception space 9 is reached, without supplying heating power from the first heat supply equipment 12 to the sample.

When a sample is introduced into the reception space 9, the temperature controller switches (manually or automatically) from the first operation mode to the second operation mode, in which the first heat supply equipment 12 and the second heat supply equipment 14 are activated in response to a temperature drop (e.g. derived from the temperature measurement signal 76 at two different time points, such as e.g. 0.5 s spaced apart). From the temperature drop, a particular heating energy may be derived which is estimated or calculated to heat the sample to the target temperature. Further, using control signals 78 and 80, the first heat supply system 12 as well as the second heat supply system 14 are controlled, in order to supply the determined heat energy to the sample. The heat energy injection by the different heat supply equipments may last only a very short time, such as less than 2, 3, or 4 s. After this injection of a particular heat energy, the temperature controller may switch (manually or automatically) back to the first operation mode.

The sensor electrodes 10 are connected to respective conductive traces 82 via through-holes through the top layer 68 which through-holes are filled with a conductive material. The conductors 82 conduct electrical signals acquired by the sensor electrodes 10 and are connected in turn to terminals 84 which allow to acquire the measurement data from the plural sensor electrodes 10 by further equipment.

The top layer 68, the first layer 65 and the second layer 66 together with the conductors placed thereon form a layer stack portion 5 of the measurement cell 3. On a back side of the layer stack portion 5 (not visible in FIG. 1 or 2), other terminals are provided that are (for example by through-holes) connected to the first conductive path 60 and the second conductive path 62 of the first heat supply equipment 12 and the second heat supply equipment 14, respectively. These terminals are connected with the output terminals of the temperature controller 74 in order to supply the control signals 78, 80.

According to an embodiment of the present invention, the first conductive path 60 may, alternatingly with heating the sample, also be operated as a temperature sensing element. In this case, the resistance of the first conductive path 60 may be measured which may be indicative of the temperature of the first conductive path 60. From the temperature of the first conductive path 60, the temperature of the sample within the reception space may be derived, for example after appropriate calibration.

In other embodiments, additionally or alternatively, a distinctive temperature sensor may be arranged within the reception space 9 in order to measure the temperature of the sample.

Figure 3:
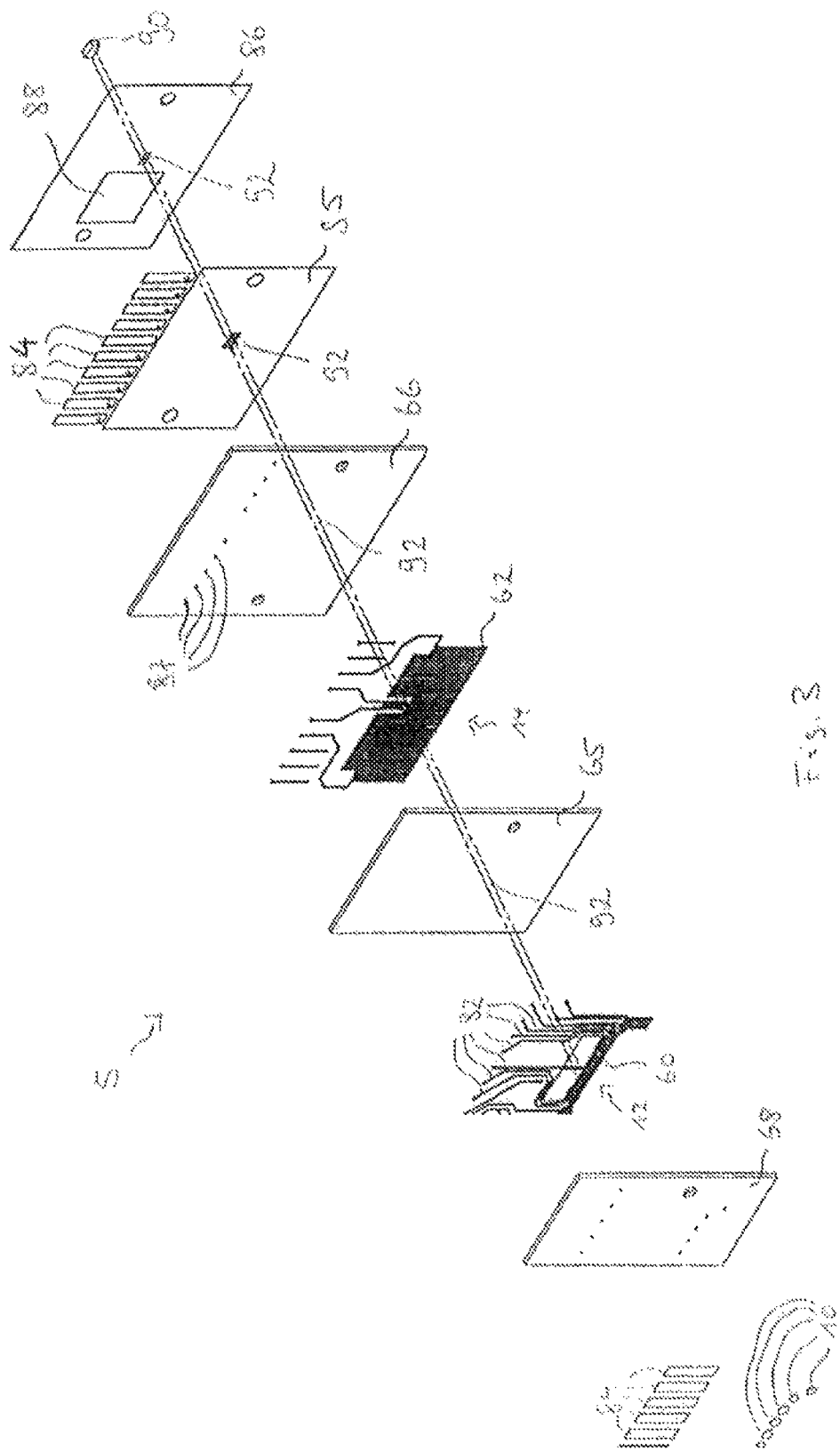
FIG. 3 illustrates schematically an explosive view of a layer stack portion of the measurement cell illustrated in FIGS. 1 and 2.

FIG. 3 illustrates in an exploded view the layer stack portion 5 of the measurement cell 3 illustrated in FIGS. 1 and 2. The sensor electrodes 10 and the terminals 84 are arranged, when assembled, on the top layer 68. The first conductive path forming the first heat supply equipment 12 is, together with the conductors 82 for conducting electrical signals of the sensor electrodes 10, arranged on the first layer 65 when the components are assembled. Further, the second conductive path 62 of the second heat supply equipment 14 is arranged on the second layer 66. The layer stack portion 5 may comprise one or more additional layers which may provide additional functions, such as e.g. electrical shielding. In the embodiment illustrated in FIG. 3, the layer stack portion 5 comprises further a layer 85 and another layer 86. The layer 85 comprises terminals 84 which may serve to supply control signals to the second heat supply equipment 14 via through-holes 87 which are arranged within the second layer 66. The other layer 86 may comprise a heat conductive pad 88 which may serve to achieve a more homogeneous temperature distribution. More or less layers than illustrated in FIG. 3 may be included within the layer stack portion 5 of the measurement cell.

The measurement cell 5 further comprises a reference temperature sensor 90 having a nominal reference resistance that is larger than a nominal resistance of the temperature sensor 60. The reference temperature sensor 90 is in good thermal contact with the layer comprising the temperature sensor 60 using conductive material filled in through holes 92 through the layers 86, 85, 66, 65.

Figure 4:
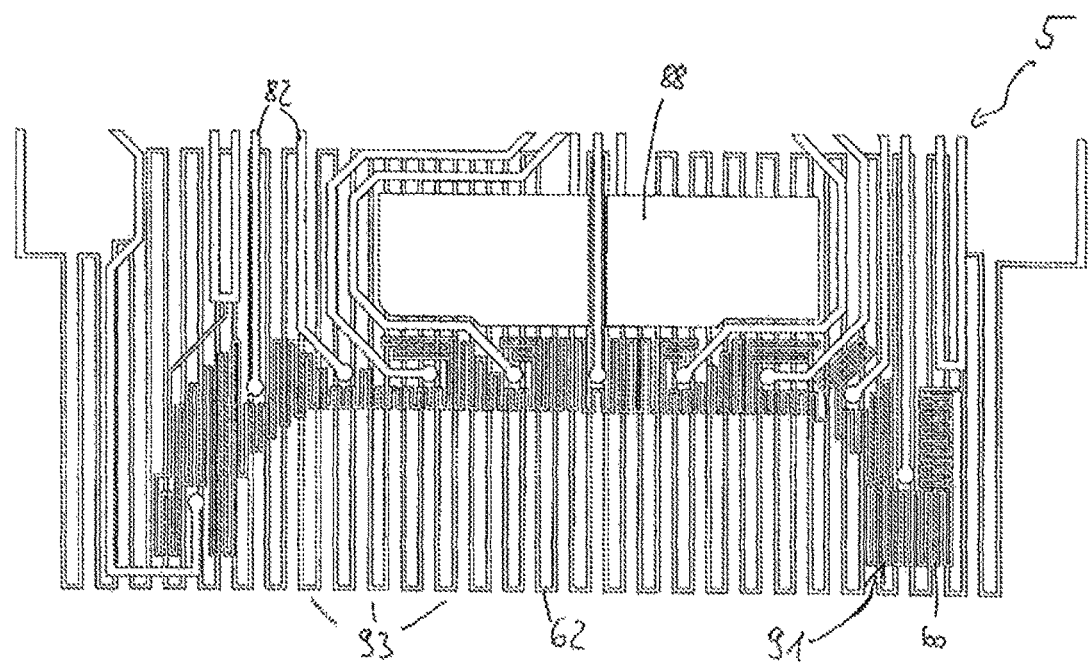
FIG. 4 schematically illustrates a plan view of a part of the layer stack portion of the layer stack illustrated in FIG. 3 in an explosive view.

FIG. 4 illustrates a plan view of a portion of the layer stack portion 5 of the measurement cell 3 illustrated in FIGS. 1 and 2. The FIG. 4 illustrates the first conductive path 60 of the first heat supply equipment as well as the second conductive path 62 of the second heat supply equipment overlaid, although in fact these two different conductive paths 60, 62 are stacked on top of each other and are vertically spaced apart from each other by the first layer 65, as is evident from FIG. 3. As can be appreciated from FIG. 4, the second area 93 which is covered by the second conductive path 62 is much larger than the first area 91 covered by the first conductive path 60. Further, the shape of the first area 91 resembles a shape of a sectional view of the reception space 9. Further, as is illustrated in FIG. 4, the second area 93 covered by the second conductive path 62 overlaps with the first area 91 covered by the first conductive path 60.

FIG. 5 schematically illustrates a measurement apparatus 1 according to an embodiment of the present invention in a perspective view including a measurement cell 3 according to an embodiment of the present invention. The measurement apparatus 1 includes a measurement cell 3 and a mounting system 6 for movably mounting the measurement cell, the mounting system 6 including a bar 21 having a guiding trail 22 and a supporting portion 23 at one end of the bar for supporting a supply needle 15.

The movable measurement cell 3 further comprises a sample supply system 11 which is (fixedly) attached to an inlet 13 at the second portion 7 of the measurement cell 3 to allow supply of a liquid sample into the reception space 9 without requiring any tubing and/or elastomeric sealing. The sample supply system 11 includes a supply needle 15 connected at one end to the inlet 13 and having a lumen in communication with the reception space 9. The reception space 9 may for example have a volume between 10 μm and 30 μm, in particular substantially or less than 20 μm.

The measurement apparatus 1 may further comprise (in FIG. 5 not illustrated) a data processing module for processing measurement data obtained from the measurement system 8, an energy supply system for providing electrical energy to components (such as the measurement system, heating equipment, temperature detection system(s)) of the measurement cell, pump(s), valve(s), a user interface, external network capability, access to a database, etc. The sample supply system 11 further comprises an elastomer element 17 having a through hole 19 through which the supply needle 15 may (partly) be inserted. The measurement apparatus 1 illustrated in FIG. 5 further comprises the mounting system 6 that includes a bar 21 having a guiding trail 22 and the mounting system 6 further comprises a supporting portion 23 at one end of the bar for supporting the supply needle 15.

In particular, the supporting portion 23 of the mounting system 6 circumferentially engages the elastomer element 17, thereby clamping the elastomer element 17 while the supply needle 15 is partly or at least partly inserted into the through hole 19 of the elastomer element 17. The supporting portion 23 prevents the supply needle 15 from bending during usage of the moveable measurement cell 3.

FIG. 5 illustrates (a part of) the measurement apparatus 1 during washing/purging and calibrating the moveable measurement cell 3. The mounting system 6 includes a guiding trail 22 on the bar 21. The second portion 7 of the moveable measurement cell 3 has a trail engagement portion 47 here formed as two protrusions protruding through a slot provided by the guiding trail 22. The movable measurement cell 3 may be moved along the guiding trail 22 along the direction 49 which corresponds to the direction 51 of a longitudinal axis of the supply needle 15. During movement of the movable measurement cell 3, the supply needle 15 penetrates through the through hole 19 of the elastomer element 17, allowing to adjust a portion of the supply needle 15 to protrude beyond the supporting portion 23 of the mounting system 6.

For supplying electrical energy to the functional elements and receiving electrical signals from the functional elements, a cable 53 is connected to respective contact terminals of the layer stack portion 5 of the moveable measurement cell 3. The contact terminals 84 may be contacted from different layers by filling through holes 87 within the layer stack portion with electrically conducting material. FIG. 5 also illustrates an outlet 57 and an inlet 58 in communication with the reception space 9. The inlet 58 may serve to supply a solution for a reference electrode.

During supply of a sample via the supply needle 15, a peristaltic pump may be connected (for example using a piping) to the outlet 57 and an end of the supply needle may be immersed in sample to be examined. The sample may then be drawn (by the action of the pump) through the lumen of the supply needle 15 into the reception space 9. Thereupon, the desired temperature (such as 37° C.) may be adjusted by controlling the heat supply equipment 12 and/or 14. As soon as the temperature has reached the desired temperature and the temperature remains constant within for example +/−0.2° C., the measurement system 8 may be operated to measure one or more constituents of the sample. If the desired temperature cannot be met within the desired period of time, the measured values relating to the fluid sample have to be converted to the target temperature by well known equations.

In particular after having activated, in particular without being feedback controlled, the second and/or the first heat supply equipment for delivering a pulse of heating energy, first heat supply equipment may be deactivated and the second heat supply equipment may be operated, in particular being feedback controlled, to generate a (substantially constant) heating power for compensating heat loss to the surrounding environment. The feedback control of the second heat supply equipment may be maintained while the measurement on the sample is performed.

Figure 6A:
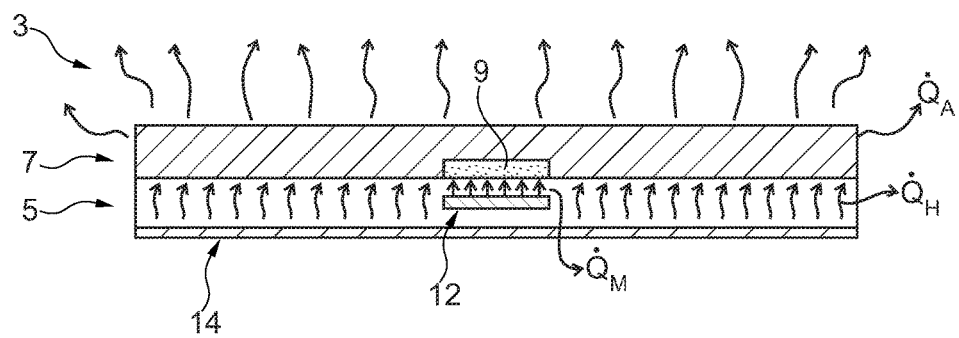
FIG. 6A schematically illustrates a measurement cell in a cross-sectional view according to an embodiment of the present invention.

FIG. 6A schematically illustrates in a cross-sectional view a measurement cell 3 according to an embodiment of the present invention. The measurement cell includes a layer stack portion 5 and a cover portion 7, the cover portion 7 partly limiting a reception space 9 within which a liquid sample is fillable. The layer stack portion 5 comprises, arranged close to the reception space 9, a first heat supply equipment 12 which is capable of generating a heat flow (e.g. area density of time derivative of flow of heat) $Q_M$. The layer stack portion further comprises a second heat supply equipment 14 extending over a larger area than the first heat supply equipment 12 and being adapted to generate a heat flow $Q_H$. The quantity $Q_A$ represents a heat flow loss to the environment.

Figure 6B:
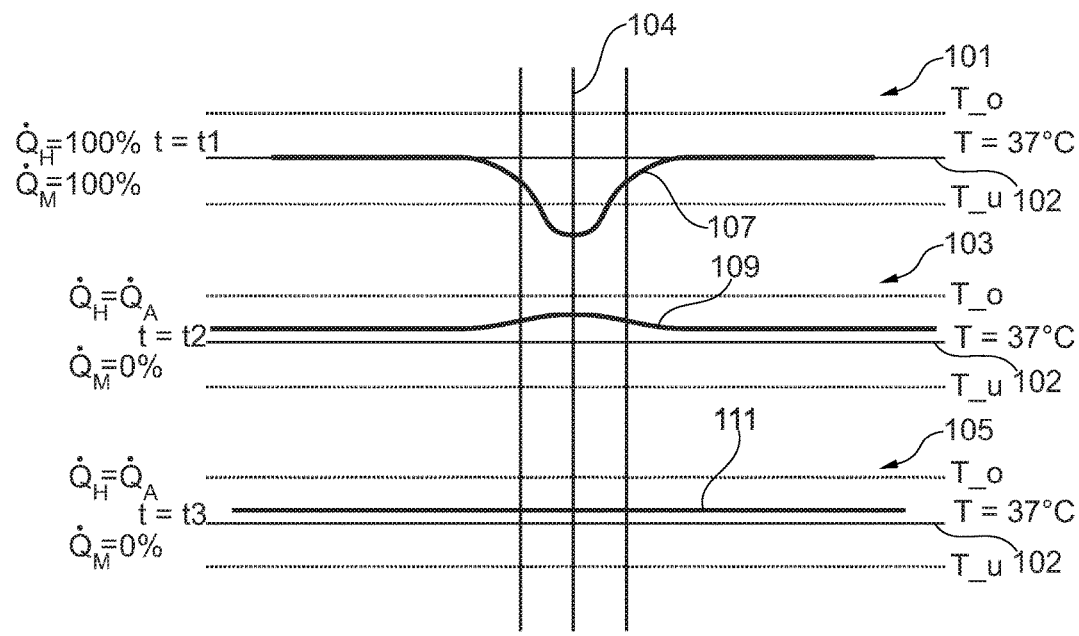
FIG. 6B illustrates graphs of a temperature profile according to an embodiment of the present invention.

The graphs 101, 103, 105 in FIG. 6B illustrate temperature profiles 107, 109, 111 for different time points t=t1, t=t2, t=t3 as observed in a method for measuring at least one constituent of a liquid sample according to an embodiment of the present invention. Thereby, the method may for example be performed using the measurement cell 3 illustrated in FIG. 6A or 1 or 2 or 3 or 5. In the graphs 101, 103, 105, the abscissa 102 denotes the coordinate x of the measurement cell 3, i.e. a lateral coordinate, while the ordinate 104 denotes the temperature.

At the time point t=t1, a liquid sample is filled into the reception space 9, wherein the measurement cell 3 had previously been equilibrated to a homogeneous temperature of t=37° C. Due to the sample being colder than 37° C., a temperature drop is observed in a region at and also around the reception space 9 illustrated by curve 107. When this temperature drop is detected, for example by a temperature sensor, such as temperature sensor 60, as is illustrated in FIG. 1, 2, 3 or 4, the heating power of the first heat supply equipment 12 may be adjusted to 100% and also the heating power of the second heat supply equipment 14 may be adjusted to 100%, for a particular time interval. During this time interval of a heat pulse, there may be no feedback control of the heat supply equipment 12 and 14. Alternatively the time interval of the heat pulse is held to a constant value and the heating power is adjusted to a value needed to supply the calculated heating energy within the time interval.

At a time t=t2, the time interval has elapsed and the heating power of the first heat supply equipment 12 is reduced to 0. The temperature profile at the time t=t2 is shown as a curve 109 in the graph 103. Between the time points t2 and t3 and after the time point t3, there is feedback control of adjusting the heating power of the second heat supply equipment 14 using temperature signals from a temperature sensor as feedback signals. Later than the time point t2, the heating power of the second heat supply equipment 14 is adjusted such that it at least substantially equal to the heat flow loss $Q_A$.

At the time point t2, the temperature at and close to the reception space 9 is slightly different (i.e. higher or lower, since the heat energy to be supplied is only estimated) than the temperature farther away from the reception space and is within a range OG and UG, wherein OG may be 37.2° C. and UG may be 36.8° C. Due to thermal conduction occurring between the time points t2 and t3, the temperature profile 101 assumes a spatially homogeneous temperature within a range OG and UG, wherein OG may be 37.2° C. and UG may be 36.8° C. Other Ranges are possible, depending on the analytes to be measured. As can be appreciated from graph 105, the temperature profile 111 is spatially homogeneous at the time point t=t3. At this time point, the measurement may be started or performed since no significant change in the temperature of the liquid filled in the reception space has to be expected.

Figure 7A:
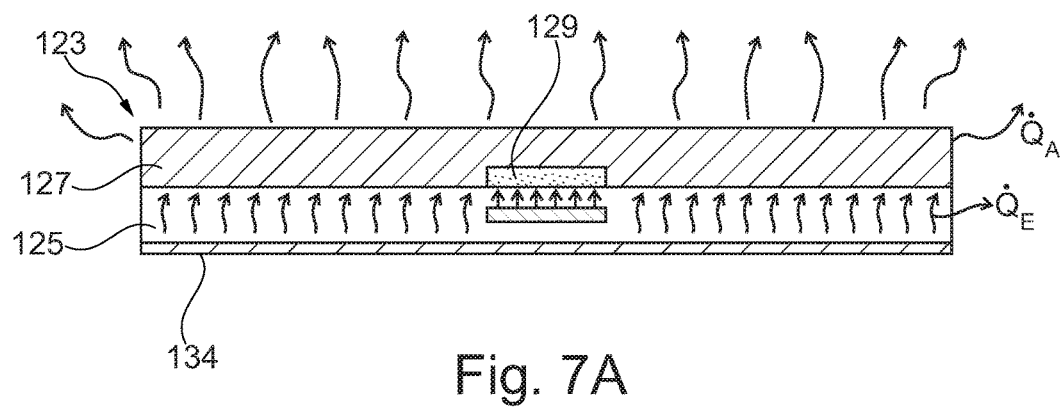
FIG. 7A illustrates in a cross-sectional view one type of a conventional measurement cell.

As a comparison, one type of a conventional measurement cell 123 is illustrated in FIG. 7A comprising a portion 127 and a portion 125 the portion 125 comprising a heater 134 heating a reception space 129. $Q_E$ denotes a heat flow of the heater 134 and $Q_A$ denotes a heat flow loss into the environment.

Figure 7B:
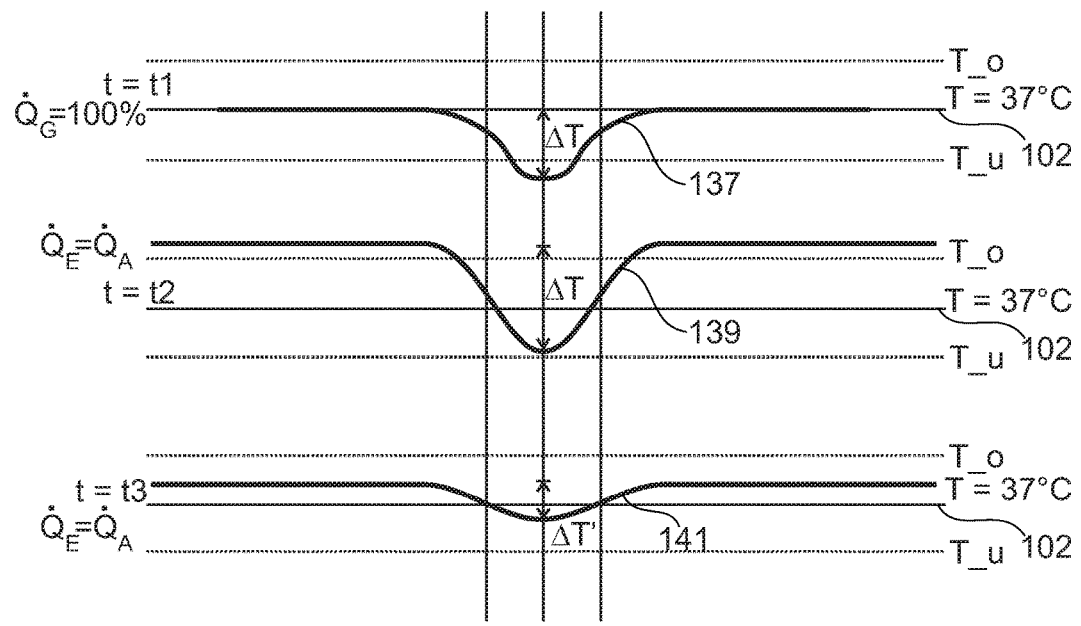
FIG. 7B illustrates temperature profiles observed for a conventional measurement cell.

FIG. 7B illustrates temperature profiles 137, 139 and 141 at different time points when using the conventional measurement cell 123. Herein, the abscissa 102 again denotes a lateral coordinate x and the ordinate 104 denotes the temperature. The temperature profile 137 again represents the temperature profile shortly after filling in a liquid sample into the reception space 129. At this time point t=t1 the heating power of the heater 134 is adjusted to for example 100%. Due to the homogeneous heating, the temperature profile 139 as observed at the time t=t2 corresponds to the temperature profile 137 shifted (by an equal amount for different lateral positions x) towards higher temperatures, affecting the degree of inhomogeneity ΔT of the temperature profile due to different thermal coefficients of the liquid sample and the portion 127. Due to lateral thermal conduction, the degree of inhomogeneity ΔT' decreases when the time point t=t3 is reached, however, there is still a considerable (in particular temporal) change of the temperature to be expected within the reception space 129, negatively affecting the accuracy of the measurement or the measurement time, in particular the temperature still deviating from the target temperature T=37° C.+/−0.2° C. for example. In contrast, embodiments of the present invention achieve to adjust and maintain the target temperature, such as T=37° C.+/−0.2° C. for example, in the reception space to a high accuracy in a shorter period of time.

The invention claimed is:

1. Measurement cell for measuring at least one constituent of a liquid sample, the measurement cell including:
   a reception space for receiving the sample;
   a measurement system having at least one sensor electrode exposed within the reception space;
   a first heat supply equipment extending over a first area;
   a second heat supply equipment extending over a second area, the first and second heat supply equipment being arranged to heat the sample within the reception space, wherein the second area is larger than the first area;
   a sample supply system attached to an inlet to allow supply of a liquid sample into the reception space, wherein the sample supply system includes a supply needle connected at one end to the inlet, the supply needle having a lumen in communication with the reception space; and
   a trail engagement portion.

2. Measurement cell according to claim 1, wherein the second area is between two times and ten times as large as the first area.

3. Measurement cell according to claim 1, wherein the first heat supply equipment is arranged closer to the reception space than the second heat supply equipment.

4. Measurement cell according to claim 1, wherein a shape of a sectional view of the reception space, at least in a region wherein the at least one sensor electrode is located, resembles a shape of the first area.

5. Measurement cell according to claim 1, wherein an area size of a sectional extent of the reception space, at least in a region where the at least one sensor electrode is located, is between 0.3 and 5 times a size of the first area.

6. Measurement cell according to claim 1,
   wherein the first heat supply equipment comprises at least one first conductive path formed in a meander shape and extending substantially in a first plane,
   wherein the second heat supply equipment comprises at least one second conductive path formed in a meander shape and extending substantially in a second plane substantially parallel to the first plane and offset from the first plane in a direction orthogonal to the first plane.

7. Measurement cell according to claim 1, wherein the measurement system comprises plural sensor electrodes arranged substantially in a sensor electrodes plane that is closer to the first plane than to the second plane.

8. Measurement cell according to claim 1, further comprising:
a temperature sensor arranged to measure a temperature related to the sample,
wherein a sensing region of the temperature sensor is located within or close to the reception space.

9. Measurement cell according to claim 1, further comprising:
a reference temperature sensor having a nominal reference resistance that is larger than a nominal resistance of the temperature sensor.

10. Measurement cell according to claim 8, wherein a sensing region of the temperature sensor is formed by the first conductive path, the first conductive path being selectively operable as heat producing or temperature measuring.

11. Measurement cell according to claim 1, wherein the sensor electrodes of the measurement system, the first conductive path and the second conductive path are formed on or in different insulating layers that are attached to each other to form a layer stack portion, the insulating layers being formed from a polymer.

12. Measurement cell according to claim 1, further comprising:
a temperature controller, adapted
to receive a temperature measurement signal from the temperature sensor,
to adjust a heating power of the first heat supply equipment and the second heat supply equipment,
wherein the temperature controller is selectively operable in a first operation mode and a second operation mode,
wherein in the first operation mode the second heat supply equipment is feedback controlled based at least on the temperature measurement signal such that a target temperature of the sample in the reception space is reached, without supplying heating power from the first heat supply equipment to the sample,
wherein in the second operation mode the first heat supply equipment and the second heat supply equipment are activated in response to a temperature drop indicated by the temperature sensor, to supply a heating energy to the sample, the heating energy being derived from a size of the temperature drop and the surrounding temperature.

13. Measurement cell according to claim 1, wherein the measurement system is adapted to perform at least one of: potentiometric measurement and amperometric measurement and conductometric measurements and optical measurements and measurements of electrical potentials and electric currents and electric impedances and absorption and optical activity and optical dichroism and fluorescence measurements.

14. Measurement cell according to claim 1, further comprising:
a cover portion connected to the layer stack portion and limiting the reception space above the layer stack portion.

15. Measurement cell according to claim 1, wherein the measurement cell is configured as a flow through cell, having an inlet and an outlet both in communication with the reception space.

16. Measurement cell according to claim 1, the sample supply system further including an elastomer element having a through hole, the supply needle being at least partially inserted into the through hole,
wherein the supply needle is adapted to penetrate the through hole of the elastomer element such as to allow supply of a sample into an end of the needle protruding from the elastomer element from a syringe or from a vacutainer,
wherein the supply needle when being partially inserted into the through hole of the elastomer element from one side allows supply of a sample from a capillary while the capillary is partially inserted into the through hole of the elastomer element from another side.

17. Measurement apparatus for measuring at least one constituent of a liquid sample, the measurement apparatus comprising: a measurement cell according to claim 1 further comprising: a mounting system for movably mounting the measurement cell, the mounting system including: a bar having a guiding trail; and a supporting portion at one end of the bar for supporting the supply needle, wherein the trail engagement portion of the measurement cell is engageable with the guiding trail for moving the measurement cell in a direction of the guiding trail being along a longitudinal direction of the supply needle.

18. Method for manufacturing a measurement cell for measuring at least one constituent of a liquid sample, the method comprising:
arranging a first heat supply equipment extending over a first area on a first insulating layer;
arranging a second heat supply equipment extending over a second area on a second insulating layer, the second area being larger than the first area;
arranging at least one sensor electrode of a measurement system on a top insulating layer;
stacking the first layer on top of the second layer;
stacking the top layer on top of the first layer; and
forming a reception space for receiving the sample above the top layer by attaching a cover portion onto the top layer such that the sensor electrode is exposed within the reception space.

19. Method for measuring at least one constituent of a liquid sample, the method comprising: receiving the sample in a reception space; heating the sample selectively using a first heat supply equipment extending over a first area and a second heat supply equipment extending over a second area, wherein the second area is larger than the first area; and measuring a property of the constituent using the measurement cell of claim 1 having at least one sensor electrode exposed within the reception space.

* * * * *